United States Patent [19]
Young

[11] 3,946,235
[45] Mar. 23, 1976

[54] HELIUM RESONANCE LAMP AND A LEAK DETECTION SYSTEM USING THE LAMP

[76] Inventor: Robert A. Young, R.R. No. 2, Loretto, Ontario, Canada

[22] Filed: Feb. 18, 1975

[21] Appl. No.: 550,561

Related U.S. Application Data

[62] Division of Ser. No. 488,184, July 12, 1974, Pat. No. 3,904,907.

[52] U.S. Cl. .............................................. 250/373
[51] Int. Cl.² .......................................... G01J 1/42
[58] Field of Search ..................... 250/373; 313/110

[56] References Cited
UNITED STATES PATENTS

| | | | |
|---|---|---|---|
| 3,493,805 | 2/1970 | Bass .................................... | 313/110 |
| 3,805,077 | 4/1974 | D'Silva et al. ................... | 250/373 X |
| 3,826,920 | 7/1974 | Woodroffe et al.................. | 250/373 |

Primary Examiner—Davis L. Willis
Attorney, Agent, or Firm—John E. Benoit

[57] ABSTRACT

A helium resonance lamp having a hollow cylindrical body including dielectric walls has a reentrant coaxial hollow element integral within said body and extending from one end thereof with an electrical conductor within said hollow element. A window partially transparent to 584A encloses the other end of said body. A hollow arm is integral with and extends from the body and contains a getter. High purity helium is maintained within the body at a pressure of 0.1 to 100 torr. The lamp is placed within a chamber connected to a vacuum system to be tested. Helium gas is sprayed near the suspected leak in the system. Helium entering the chamber from the system is detected and displayed.

4 Claims, 2 Drawing Figures

U.S. Patent   March 23, 1976   3,946,235

HELIUM RESONANCE LAMP AND A LEAK DETECTION SYSTEM USING THE LAMP

This is a division of application Ser. No. 488,184, filed July 12, 1974, now U.S. Pat. No. 3,904,907.

The present invention relates broadly to apparatus for and a method of leak detection in vacuum systems. More specifically, the invention relates to a helium resonance lamp and a system using such a lamp for such leak detection.

Available means for detecting small leaks in vacuum systems require high vacuum pumping. This results in the necessity of large and relatively expensive equipment.

It is an object of this invention to provide a helium resonance lamp.

It is a further object of this invention to provide a means for determining small leaks in a vacuum system using a helium resonance lamp.

Yet another object of this invention is to provide a small, light weight device for detecting small leaks in a vacuum system.

Figure 1:
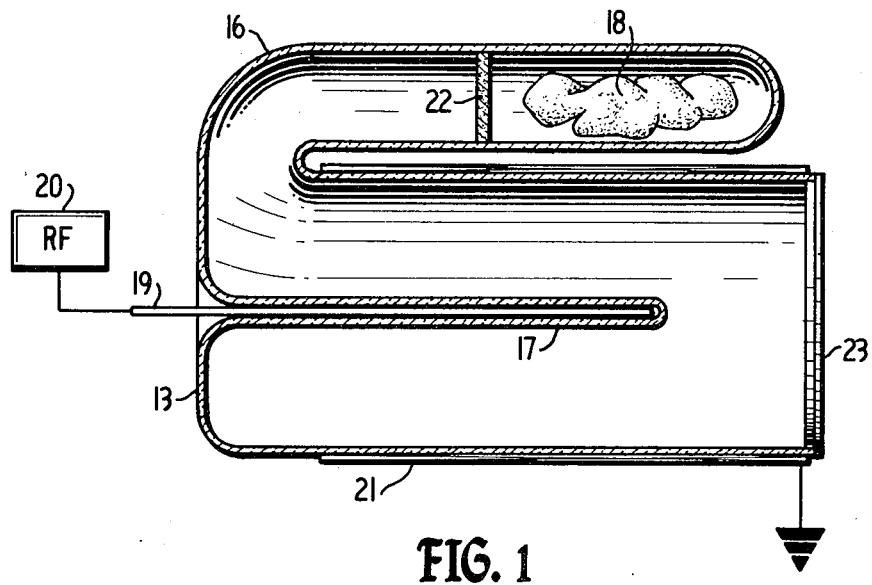
Figure 2:
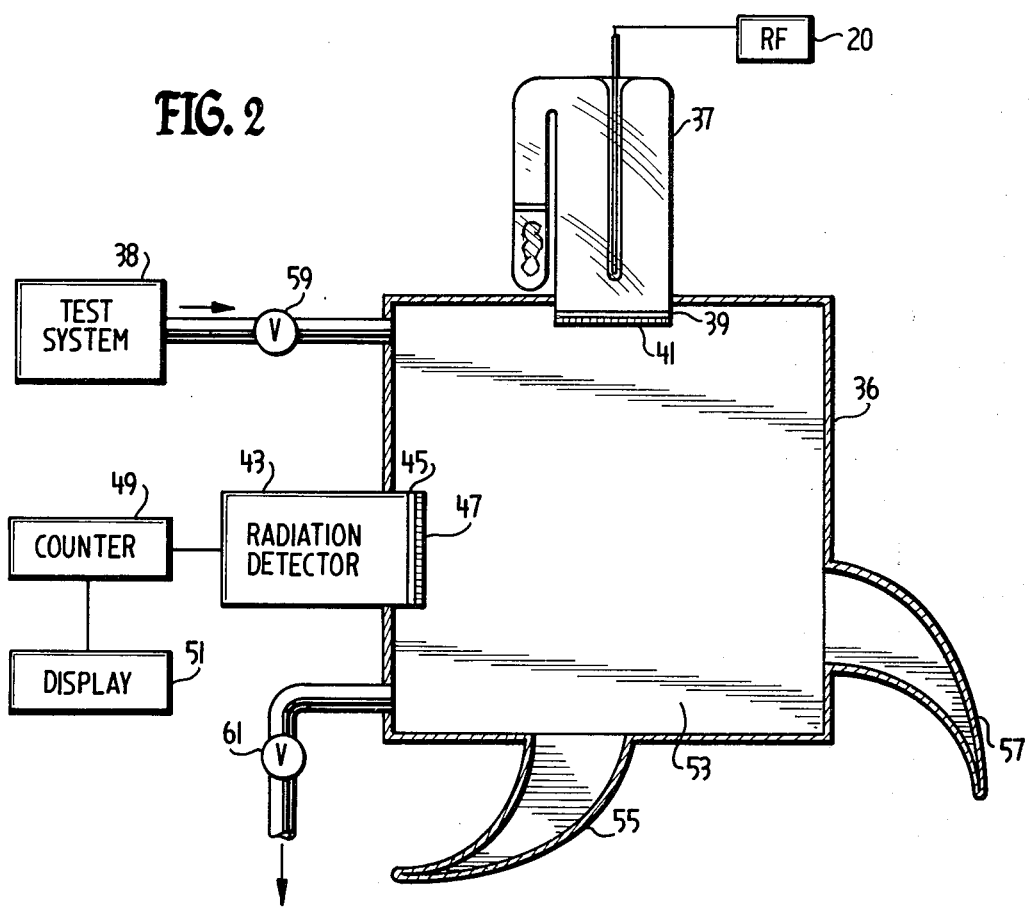

These and other objects will become apparent from the following description taken together with the drawings wherein:

FIG. 1 is a schematic view of a cross-section of the helium resonance lamp of the present invention; and FIG. 2 is schematic illustration of the leak detection system of the present invention.

Turning now to FIG. 1 there is shown therein a preferred embodiment of a helium resonance lamp used in the present invention. The basic structure of the lamp is described in U.S. Patent application Ser. No. 426,616 now U.S. Pat. No. 3,851,214, entitled Low Power Sealed Optically Thin Resoncance Lamp, filed in the name of the present inventor.

Basically, the lamp 11 comprises a hollow cylindrical body 13 having a dielectric wall, such as glass, with a reentrant coaxial hollow glass element 17 located centrally within body 13. An electrical conductor 19 is connected to a source of RF energy 20. An integral arm 16 extends from cylindrical body 13 and contains a material 18 which acts as a getter such as uranium or barium. A gas permeable filter 22 such as glass frit maintains material 18 in position. Cylindrical body 13 is filled with high purity helium and a thin window 23, preferably of aluminum, is provided so as to pass only the desired radiation.

Window 23 is partially transparent to 584A radiation. The helium gas within cylindrical body 13 is maintained at a pressure between 0.1 and 100 torr.

Thus, there is provided a helium resonance lamp having an emission at substantially 584A with a thin, i.e. $\approx$ 1,000A, window partially transparent to 584A radiation. The window 23 is designed so as to be able to withstand high pressure when immersed in a gas mixture such as a mixture wherein one of the components is helium at a pressure between 0.1 and 100 torr.

The cylindrical body may be covered by an electrically conductive material 21 which is electrically grounded as is schematically shown. An example of a means for accomplishing this is when cylindrical lamp body 13 is enclosed within a close fitting conductive housing which is grounded. Therefore, the lamp body is effectively sheathed by a grounded conductive element. This element completes the necessary path for electrical excitation by RF source 20.

When lamp 11 is electronically excited by the RF source 20, helium radiation is passed by the window and absorbed by He outside the lamp and, subsequently, this energy is either radiated at 584A or transferred from the helium to other components of the gas mixture. This transfer may occur either directly, or through collisions of electronis, whose energy has been increased by superelastic interactions with excited helium, or as a consequence of ion neutralization (either with a free electron or with an attached electron in the form of a negative ion). For use in a He leak detector re-emission of 584A radiation predominates because of the low pressure outside the lamp window.

Of the materials which pass 584A, aluminum is preferred for practical reasons.

Turning now to FIG. 2 there is shown a system using the helium resonance lamp of FIG. 1 in a helium leak detecting system.

The helium lamp 37 is mounted so that the aluminum window 39 extends within a gas chamber 36. The gas chamber is connected to the system 38 which is to be subjected to the testing for leaks therein. In the usual manner, the system is subjected to helium gas which is sprayed near possible leak locations in the system. The output of the system under test is connected by valve 59 to the chamber 36 and by valve 61 to an exhaust system. If the system is such that it should require a vacuum pumping system, such a system could be connected to the output of valve 61.

Also mounted for viewing purposes in the wall of chamber 36 is a helium resonance radiation detector 43, such as an aluminum windowed geiger counter or photomultiplier. The output of the detector 43 is supplied to a counter 49 whose output is then displayed by device 51 which may be either visual or aural, or both.

The helium lamp 37 projects helium resonance radiation at 584A through a collimator 41 adjacent the aluminum window 39 to the scattering volume within the gas chamber 36. If there is helium present in the gas supplied from the test system it will be detected by its scattering of 584A radiation, which is measured by detector 43. The output pulses from this detector is counted by counter 49 for a fixed time (approximately 1 to 100 seconds) and the photon detection rate may then be displayed by display device 51. The higher the count rate the more helium there is in the scattering volume within the gas chambers 36.

Both the resonance lamp 37 and the detector 43 are part of the vacuum scattering chamber wall which constitutes the chamber 36. This chamber also has light traps 55 and 57 opposite the lamp and the detector respectively.

The helium leak detector of FIG. 2 replaces a standard high vacuum pump, and mass spectrometer, with a helium ion detector which are usually used when applying the helium leak detection method.

The system of FIG. 2 possesses numerous advantages over the previous known methods of detecting small leaks in vacuum systems such as the ability to operate at much higher pressures than the presently used techniques. Further there is no high vacuum pumping requirement and the device is less expensive and contains more reliable components. Additionally, the device is of a smaller size and lighter in weight which provides a greater portability. The device of the present invention also has high sensitivity when used in a continuous pump mode and a much higher sensitivity when used in the closed off pressure build up mode.

The above description and drawings are illustrative only since equivalents could be substituted without departing from the invention. Accordingly, the invention is to be limited only by the scope of the following claims.

I claim:
1. Apparatus for detecting gas leaks by the helium leak method in a system comprising
   a helium resonance lamp having an emission at 584A;
   a window in said lamp partially transparent to 584A radiation;
   a helium resonance radiation detector;
   a chamber incorporating said helium lamp and helium resonance radiation detector;
   means for supplying RF power to the He lamp; and
   means connected to said detector for displaying the output from said detector.
2. The apparatus of claim 1 wherein said window is aluminum.
3. The apparatus of claim 1 wherein said lamp comprises
   a hollow cylindrical body having a dielectric wall;
   a reentrant coaxial hollow element integral within said body and extending from one end thereof substantially the length of said body;
   an electrical conductor within said hollow element;
   said window being located at the other end of said body;
   a hollow arm integral with and extending from said body;
   a getter in said hollow arm for removing gases from said body;
   high purity helium within said body at a pressure between 0.1 and 100 torr; and
   a grounded electrically conductive sheath surrounding said body.
4. The apparatus of claim 3 further comprising
   means for connecting an RF source to said electrical conductor.

* * * * *